United States Patent [19]

Wright

[11] Patent Number: 4,973,300
[45] Date of Patent: Nov. 27, 1990

[54] CARDIAC SLING FOR CIRCUMFLEX CORONARY ARTERY SURGERY

[75] Inventor: John T. M. Wright, Conifer, Colo.

[73] Assignee: Pioneering Technologies, Inc., Wheat Ridge, Colo.

[21] Appl. No.: 411,317

[22] Filed: Sep. 22, 1989

[51] Int. Cl.⁵ .............................................. A61F 13/00
[52] U.S. Cl. ....................................................... 600/37
[58] Field of Search ...................... 600/37; 128/94, 155

[56] References Cited

U.S. PATENT DOCUMENTS

| | | | |
|---|---|---|---|
| 3,983,863 | 10/1976 | Janke et al. ............................ | 600/37 |
| 4,217,890 | 8/1980 | Owens .................................... | 600/37 |
| 4,271,828 | 6/1981 | Angelchik ............................. | 600/37 |
| 4,403,604 | 9/1983 | Wilkinson et al. .................... | 600/37 |
| 4,637,377 | 1/1987 | Loop ...................................... | 600/37 |

Primary Examiner—Robert A. Hafer
Assistant Examiner—Kerry Owens
Attorney, Agent, or Firm—Grant L. Hubbard

[57] ABSTRACT

A cardiac sling for supporting the heart during surgery a support a polymeric film net of interconnecting ribs of polymeric material for applying, in use, sufficient pressure to the portions of the surface of the heart adjacent the ribs to prevent hemorrhage from the anastomotic site of bypass grafting is disclosed.

7 Claims, 2 Drawing Sheets

CARDIAC SLING FOR CIRCUMFLEX CORONARY ARTERY SURGERY

BACKGROUND OF THE INVENTION

This invention relates to an improved cardiac sling for supporting the heart and providing cardiac exposure for surgery to the circumflex branch of the coronary artery.

Coronary bypass surgery of the circumflex coronary artery is difficult because the vessel lies on the posterior surface of the heart. The field is made accessible by arresting and draining, and then lifting and partially rotating the heart. Several methods have been used to achieve the required exposure. An assistant may hold the heart with outstretched hand. This can be inconvenient for several reasons. Of importance is that an assistant is required. In some cardiac centers, where an assistant is not used, this method is inappropriate. The assistant's hand in the operative field can get in the way, and the assistant, who often stands adjacent to the surgeon, may restrict the surgeon's movements. The assistant often does not have a clear view of the heart, and often finds the process tiring. The heat from the assistant's hand will warm the hypothermic heart in the area of digital pressure. This digital pressure can cause bruising of the heart.

The use of a neat was described by R. W. M. Frater, "Yet another technique for exposing the circumflex coronary artery" Am. J. Surg. 133, 650–651, 1977. This method has the merit of low cost, but the fine strands impinge on the heart and potentially can cause damage.

A heart support for coronary artery surgery was described in U.S. Pat. No. 3,983,863 (Janke, W. H. and Barron, M.). This heart support was formed of flat clotch tapes crossing each other at right angles and attached together to provide a mesh with square openings. The disadvantage of this device is that the cloth has a rough texture that can abrade the heart. The device is relatively inelastic, and cannot therefore support the heart in a uniform manner. In addition, the squares formed between the tapes are rather large, while the area of the heart lying under the tapes are not visible to the surgeon.

A later device was described by Angelini, G. D. "A simple, inexpensive method of heart retraction during coronary bypass surgery" Ann. Thorac. Surg. 46, 246, 1988. The method has the merit of simplicity, low cost and good exposure, but has the disadvantage that the supported weight of the heart is carried over a small area, which may cause damage to the myocardium.

A further consideration in coronary artery surgery is hemorrhage from the incision into the coronary artery at the proposed anastomotic site. Coronary artery surgery is usually carried out under conditions of cardiac arrest and aortic root cross clamping. Hence the myocardium is temporarily deprived of coronary blood supply. In some patients, an additional coronary blood supply, through to be from bronchial circulation, causes significant hemorrhage during the bypass grafting process. This hemorrhage is both inconvenient, as it masks the surgeon view during the delicate suturing process, and threatens the well-being of the patient.

An objective the present invention is an improved cardiac sling providing a substantially uniform support over the contacted surface of the heart.

A further objective of the present invention is to provide an unobstructed view of the heart to the surgeon.

A further objective of the present invention is to constrict unwanted coronary circulation to minimize hemorrhage from the anastomotic site during coronary bypass grafting.

SUMMARY OF THE INVENTION

The cardiac sling is formed of a flat sheet of transparent elastomeric material which defines a supporting portion having a multiplicity of hexagonal shaped holes separated by rigs between the holes. The ribs between the hexagonal holes are of appropriate width to restrict unwanted coronary blood flow while preventing high contact pressures on the surface of the heart. The support portion of the sling is approximately rectangular in shape and has tapes formed integrally therewith having parallel free ends extending longitudinally from one of the support portion sling. The tapes position the support portion of the sling under the heart and for maintaining the heart in the chosen position by being threaded through appropriate hexagonal holes in the support portion of the sling before being clamped to the surgical drapes.

In a preferred embodiment, the invention comprises a cardiac sling for supporting the heart during surgery which comprises a support portion in the form of a polymeric film net of interconnection ribs of such polymeric material for applying, in use, sufficient pressure to the portions of the surface of the heart adjacent the ribs to prevent hemorrhage from the anastomotic site bypass grafting and means for securing the support portion under the heart. The polymeric net film preferably comprises a multiplicity of holes surrounded by said interconnecting ribs, the holes preferably being hexagonal in shape, the ribs defining six sides thereof. The hexagonal holes are preferably from about 0.25 to about 0.75 inch as measured between opposed flat sides of the hexagonal holes separated by ribs from about 0.062 to about 0.312 inches wide. The polymeric material is preferably transparent lightly colored blue or a color which contrasts with blood and tissue and, in the preferred embodiment is between about 0.005 and about 0.030 inches in thickness, soft and smooth with a matt finish. Tear resistant, blood impervious polyurethane being the preferred material.

The invention will be better understood, and additional advantages will become apparent from the following description of the preferred embodiment illustrated on the accompanied drawings.

DESCRIPTION OF THE PREFERRED EMBODIMENT

Figure 1:
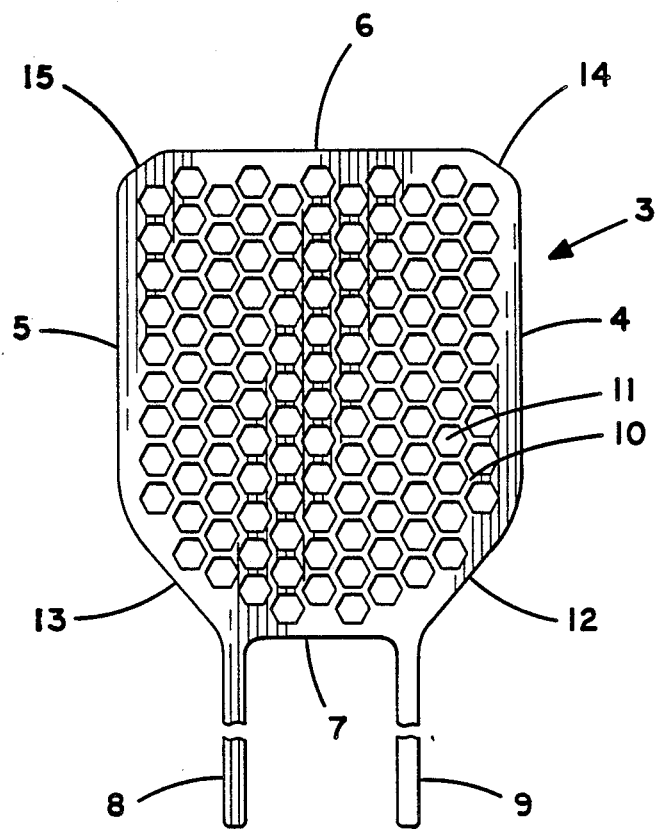
FIG. 1 is a plan view of the sling, portions of the tapes being omitted to better illustrate the support portion of the sling in an easily visible scale.
Figure 2:
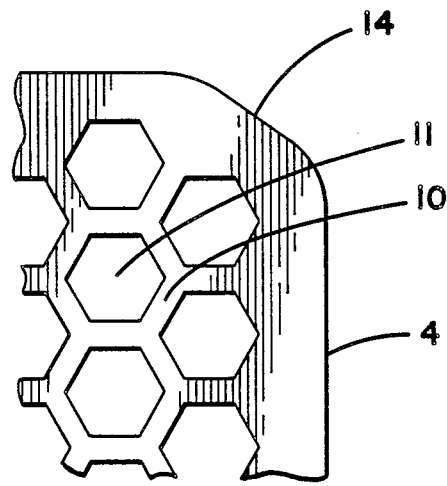
FIG. 2 is a fragmentary perspective view of a portion of the support portion to the sling near one distal corner.

The support portion of the sling 3 comprises parallel first and second sides 4 and 5, distal end 6 and proximal end 7. Two parallel narrow tapes 8 and 9 extend from the proximal end of the support portion a distance from one to two times the length of the support portion.

The support portion comprises a latticework of ribs 10 surrounding a multiplicity of hexagonal holes 11 formed in the elastomeric film sheet. The sides 4 and 5 of the support portion taper from about one-fifth the length of the sheet toward each other to the proximal end of the support portion of the sling, as shown at 12 and 13. The corners of the sheet at the distal end, 14 and 15, are cut so as to avoid sharp angles by, for example, cuttings corners to a radius of a circle or an ellipse, or forming a short linear portion on the edge with a radius cut to the respective and side of the support portion.

Figure 4:
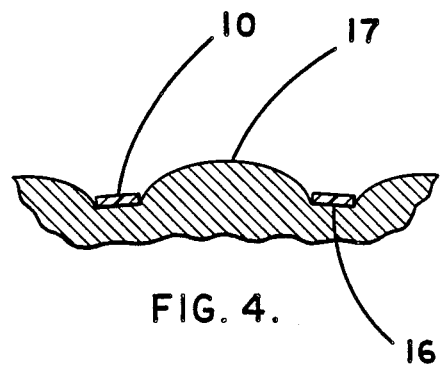
FIG. 4 is a cross-sectional view or a portion of the myocardium and ribs of the support portion of the sling.
Figure 3:
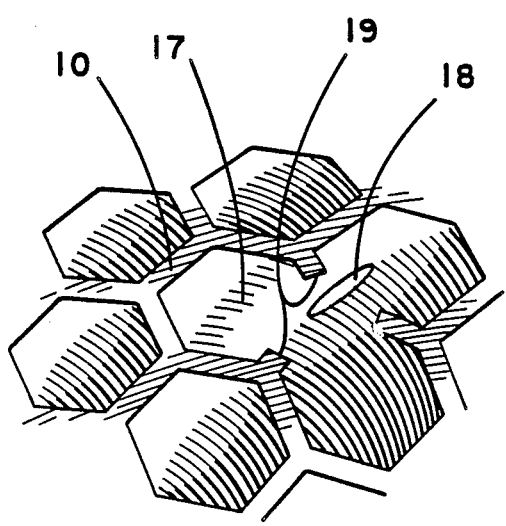
FIG. 3 is a fragmentary view of the site of the coronary anastomosis, with view-obstructing ribs of the support portion being cut away.

In the preferred embodiment, the cardiac sling is die cut from a biocompatible, tear resistant, lightly colored, transparent elastomeric film. The "net" of the support portion is formed by die cutting a multiplicity of hexagonal holes 11 leaving interconnecting ribs 10, the resulting net conforming to the shape of and supporting the myocardium when the sling is used, as shown in FIG. 3. The ribs 10 of the net form multiple pressure points 16 on the myocardium 17 as shown in FIGS. 3 and 4, restricting unwanted coronary blood flow and reducing the tendency for hemorrhage at the anastomotic site such as depicted at 18 in FIG. 3. The sling is symmetrical about a longitudinal axis extending between the tapes parallel to and equidistant from the sides 4 and 5 of the support portion. The two smooth integrally formed extension tapes 8, 9 permit easy insertion thereof through the transverse sinus and beneath the inferior vena cava, respectively, and through the hexagonal openings in the net formed in the support portion and good retention therein. The sling is formed of a soft, smooth, matt finish polyurethane, which is tear resistant and impervious to blood, and transparent, permitting the surgeon to see therethrough, and is colored, preferably a light blue, so that it can easily be seen against the surface of the heart.

The support portion is generally from about five to 8 inches wide and from six to nine inches long, though these dimensions are not at all critical. The tapes are from about eight to fifteen inches long, the length not being in the least critical so long as they are long enough to perform the function indicated.

Figure 5:
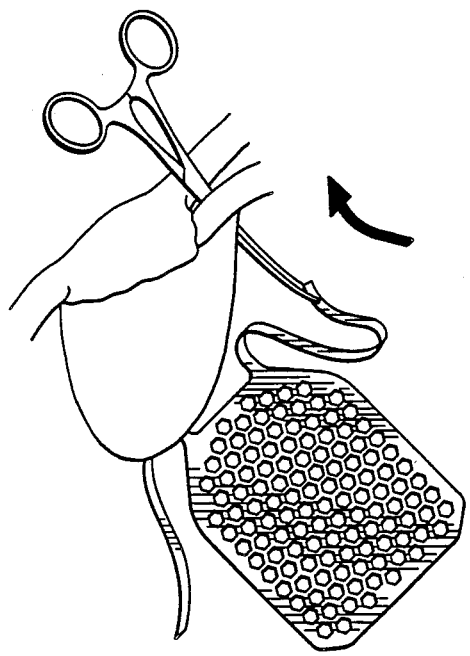
FIG. 5 depicts the sling in use, one of the tie tapes being pulled through the transverse sinus under the aorta and pulmonary artery.
Figure 6:
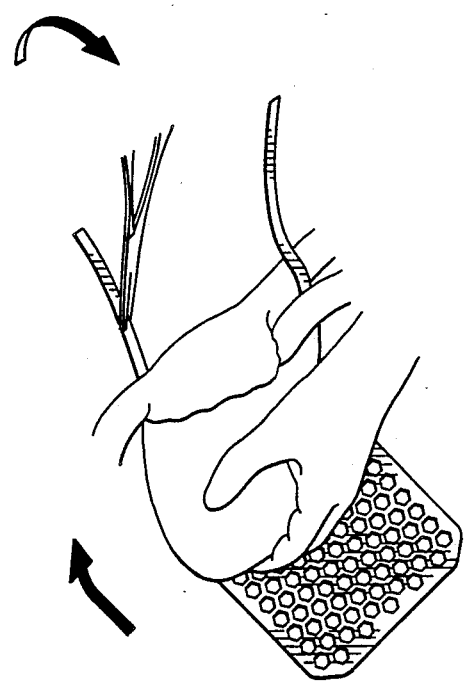
FIG. 6 depicts the sling in use, the other tie tape being pulled under the heart immediately beneath the inferior vena cava.
Figure 7:
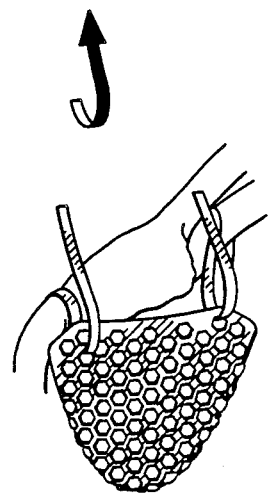
FIG. 7 depicts the sling in use, both tapes being pulled until the edge of the support portion of sling lies against the left atrium and being threaded through two holes in the support portion of the sling.
Figure 8:
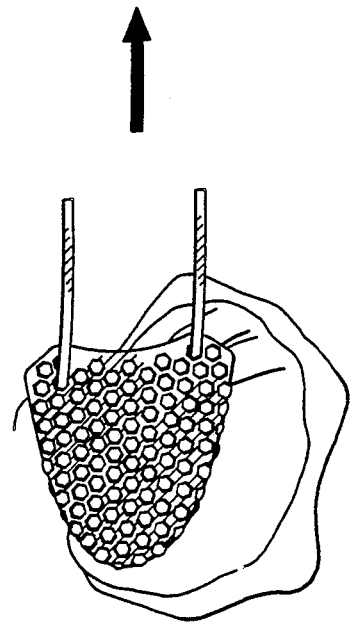

In use, the support portion of the sling is positioned under the heart as follows. Using curved forceps, one of the sling's tapes 8 is pulled through the transverse sinus under the aorta and pulmonary artery (so that he tape passes from the patient's left to right), behind the left atrium, as depicted in FIG. 5. The apex of the heart is then lifted, and again using curved forceps, the other tape is pulled under the heart immediately beneath the inferior vena cava, as depicted in FIG. 6. A simultaneous pull is applied on the two tapes until the edge of the support portion of the sling, adjacent to the two tapes, lies against he left atrium, and the ends of the tapes are then threaded through two appropriate holes close to the exposed edge of the support portion of the sling and pulled upwards and towards the surgeon, as depicted by the arrows in FIGs. 7 and 8, and clamped to the surgical drapes. Should one or more webs of the support portion of the sling obstruct the site of the proposed anastomosis, the obstructing ribs of the support portion are easily identified and can be cut away and removed, as shown at 19 in FIG. 3.

At the conclusion of the circumflex surgery (especially when the internal mammary artery has been utilized or when the aorta-saphenous anastomosis has already been completed), the support portion of the sling is cut across past the anastomotic site for easy removal.

In a specific preferred embodiment, the support portion is formed of soft, smooth, tear resistant, blood impervious transparent polyurethane film colored with a color which contrasts with the color of tissue and blood and having a matt finish, the film being between about 0.005 and about 0.030 inches in thickness, having a multiplicity of hexagonal holes therethrough having a diameter of from about 0.25 to about 0.75 inch, as measured between opposed flat sides thereof, separated by interconnecting ribs from about 0.062 to about 0.312 inches wide which define the six sides of the hexagonal holes, thereby forming a net of interconnecting ribs for applying, in use, sufficient pressure to the portions of the surface of the heart adjacent the ribs to prevent hemorrhage from the anastomotic site by bypass grafting.

Several significant advantages of the invention over the slings previously used will be apparent from the foregoing description. The support portion conforms almost perfectly with the configuration of the myocardium, stretching in all directions as required, an provides a multiplicity of pressure points or pressure lines along the ribs which apply a uniform pressure thereby restricting unwanted coronary blood flow reducing the tendency to anastomotic site hemorrhaging without applying damaging pressure on portions of the myocardium. The sling, being lightly colored and transparent, gives a better view of the myocardium to the surgeon and yet stands out so as to be plainly visible because it will not absorbed blood and become virtually indistinguishable from the heart tissue as is the case when fabric devices are used. The device adapts to the size of the heart by conforming thereto and by providing a multiplicity of holes in the support portion through which the tapes may pass.

Industrial Application

The invention is useful in human and animal surgery.
What is claimed is:

1. A cardiac sling for supporting the heart during surgery comprising:
a support portion comprising a latticework of ribs surrounding a multiplicity of holes formed in an elastomeric film sheet, the lattice work being so constructed an configured such that the holes have a minimum diameter of from about 0.25 to about 0.75 inch and the ribs are from about 0.062 to about 0.312 inches wide as to apply, sufficient pressure to the portions of the surface of the heart adjacent there is to prevent hemorrhage from the anastomotic site by bypass grafting;
and means for securing the support portion under the heart.

2. The cardiac sling of claim 1 wherein the elastomeric film sheet is formed of transparent polymer lightly colored a color which contrasts with blood and tissue.

3. The cardiac sling of claim 1 wherein the elastomeric film sheet is formed of polymeric material between about 0.005 and about 0.030 inches in thickness.

4. The cardiac sling of claim 1 wherein the elastomeric film sheet is formed of soft, smooth, matt finish, tear resistant, blood impervious polyurethane.

5. The cardiac sling of claim 1 wherein the means for securing the support portion under the heart comprises at least a pair of tapes extending from the support portion, at the support portion and tapes being formed of one unitary sheet of said polymeric film.

6. A cardiac sling for supporting the heart during surgery comprising:

a support portion formed of soft, smooth, tear resistant, blood impervious transparent polyurethane colored with a color which contrasts with the color of tissue and blood having a matt finish between about 0.005 and about 0.030 inches in thickness, having a multiplicity of hexagonal holes having a diameter of from about 0.25 to about 0.75 inch as measured between opposed flat sides thereof separated by interconnecting ribs from about 0.062 to about 0.312 inches wide defining six sides thereof forming a net of said interconnecting ribs for applying, in use, sufficient pressure to the portions of the surface of the heart adjacent the ribs to prevent hemorrhage from the anastomotic site of bypass grafting;

and means for securing the support portion under the heart.

7. A cardiac sling for supporting the heart during surgery comprising:

a support portion formed of soft, smooth, tear resistant, blood impervious transparent polyurethane film colored with a color which contrasts with the color of tissue and blood and having a matt finish, thefilm being between about 0.005 and about 0.030 inches in thickness, having a multiplicity of hexagonal holes having a diameter of from about 0.25 to about 0.75 inch as measured between opposed flat sides thereof separated by interconnecting ribs from about 0.062 to about 0.312 inches wide defining six sides thereof forming a net of said interconnecting ribs for applying, in use, sufficient pressure to the portions of the surface of the heart adjacent the ribs to prevent hemorrhage from the anastomotic site of bypass grafting;

and at least a pair of tapes extending from the support portion for securing the support portion under the heart;

the support portion and tapes being formed of one unitary sheet of said polyurethane film.

* * * * *